United States Patent
Franczyk, II

(10) Patent No.: US 6,441,223 B1
(45) Date of Patent: Aug. 27, 2002

(54) METHOD OF MAKING PHOSPHORUS-CONTAINING COMPOUNDS AND PRODUCTS THEREOF

(75) Inventor: Thaddeus S. Franczyk, II, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/728,577

(22) Filed: Nov. 30, 2000

(51) Int. Cl.$^7$ ............................. A01N 57/20; C07F 9/38
(52) U.S. Cl. ................... 562/24; 558/108; 558/110; 558/111; 558/169; 558/138; 504/206; 562/16; 562/17
(58) Field of Search ................... 558/169, 108, 558/110, 111, 138; 562/17, 16, 24; 504/206

(56) References Cited

U.S. PATENT DOCUMENTS

| | | |
|---|---|---|
| 3,784,590 A | 1/1974 | Firestone |
| 3,799,758 A | 3/1974 | Franz |
| 3,907,652 A | 9/1975 | Wagenknecht et al. |
| 3,969,398 A | 7/1976 | Hershman |
| 4,072,706 A | 2/1978 | Hershman et al. |
| 4,264,776 A | 4/1981 | Hershman et al. |
| 4,348,332 A | 9/1982 | Oediger et al. |
| 4,405,531 A | 9/1983 | Franz |
| 4,568,432 A | 2/1986 | Rogers |
| 4,624,937 A | 11/1986 | Chou |
| 4,937,376 A | 6/1990 | Fields, Jr. et al. |
| 5,023,369 A | 6/1991 | Fields, Jr. |
| 5,043,475 A | 8/1991 | Fields, Jr. |
| 5,047,579 A | 9/1991 | Glowka et al. |
| 5,072,033 A | 12/1991 | Fields, Jr. et al. |
| 5,693,593 A | 12/1997 | Arnold |
| 5,703,273 A | 12/1997 | Stern et al. |
| 5,912,209 A | 6/1999 | Kassebaum et al. |
| 5,935,905 A | 8/1999 | Mito |
| 5,985,794 A | 11/1999 | Hasebe et al. |
| 5,994,269 A | 11/1999 | Bugg et al. |
| 5,998,332 A | 12/1999 | Sato et al. |
| 6,054,608 A | 4/2000 | Franczyk, II |
| 6,083,878 A | 7/2000 | Brants et al. |

FOREIGN PATENT DOCUMENTS

| | | | |
|---|---|---|---|
| GB | 1076244 | * | 7/1967 |
| JP | 6-157399 | | 6/1994 |
| WO | WO 009519 A1 | | 2/2000 |

OTHER PUBLICATIONS

H. Gross, Synthesis and Use of Formylphosphonate Acid Derivatives, Session Report of the Adw German Democrat Republic, vol. 14, 1979.

Wagenknecht et al., A One–Step Synthesis of Aminomethylphosphonic Acid, Syn. React. Inorg. Met.–Org. Chem., vol. 12(1), pp. 109, 1982.

Livantsov et al., Phosphorylation of Orthoformates, Plenum Publishing Corp., p. 811, 1982.

Hamilton et al., The Reaction of DimethylDioxirane with Diazomethylphosphonates; the First Synthesis of a Formylphosphonate Hydrate, J. Chem. Soc. Chem. Commun., pp. 37–38, 1994.

Sawyer et al., Metal [Mlx; M×Fe, Cu, Co, Mn]/Hydroperoxide–Induced Activation of Dioxygen for the Oxygenation of Hydrocarbons–Oxygenated Fenton Chemistry, Acc. Chem. Res., vol. 29, pp. 409–416, 1995.

J. March, Advanced Org. Chemistry: Reactions, Mechanisms, and Structure, John Wiley & Sons $3^{rd}$ Ed., pp. 628–629, 1985.

Alt et al., Electrochemical Oxidation of Alpha Amino and Alpha Hydrazino Phosphinic Acids, Syn. React. Inorg. Metal–Org. Chem., vol.4(3), pp. 255–262, 1974.

Wagenknecht, An Electrochemical Method for the Preparation of Iminodimethylenediphosphonic Acid, Syn. React. Inorg. Metal–Org. Chem., vol. 4(6), pp. 567–572, 1974.

Wagenknecht, Electrochemical Oxidation of N–Substituted Iminodimethylenediphosphonic Acids, J. Electrochem. Soc.: Electrochemical Science and Technology, vol. 123(5), pp. 620–624, May 1976.

Stover et al., Determination of Organic Phosphonates by Isotachophoresis, Analytica Chim. Acta., vol. 135, pp. 347–350, 1982.

Cairns et al., The Synthesis and Chemistry of Formylphosphonate, Phosphorus, Sulfur Silicon Relat. Elem., vol. 144–146, pp. 385–388, 1999.

Hamilton et al., Reactions of Diazomethylphosphonate: The First Synthesis of a Formylphosphonate Hydrate, Phosphorus, Sulfur, and Silicon, vol. 109–110, pp. 441–444, 1996.

* cited by examiner

Primary Examiner—Joseph K. McKane
Assistant Examiner—Ebenezer Sackey
(74) Attorney, Agent, or Firm—Jenkens & Gilchrist A Professional Corporation

(57) ABSTRACT

A process for oxidizing a hydroxymethylphosphonic acid compound to produce a formylphosphonic acid compound is described. The oxidation reaction is carried out in the presence of an oxidant and a catalyst. For example, hydroxymethylphosphonic acid (HMPA) is oxidized by oxygen or hydrogen peroxide in the presence of a copper-containing catalyst to give formylphosphonic acid (FPA). Formylphosphonic acid can then be reacted with glycine to produce a condensation product which, upon hydrogenation, yields glyphosate. Glyphosate can be incorporated into various formulations for use as a herbicide. In addition to glycine, formylphosphonic acid can also be reacted with ammonia, ethanolamine, or other primary amines to form a precursor compound, which can be converted to glyphosate.

42 Claims, 2 Drawing Sheets

METHOD OF MAKING PHOSPHORUS-CONTAINING COMPOUNDS AND PRODUCTS THEREOF

PRIOR RELATED APPLICATION

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to the preparation of formylphosphonic acid and its related compounds. The invention also relates to a method of making glyphosate, its related compounds, and products thereof.

BACKGROUND OF THE INVENTION

N-phosphonomethylglycine, also known as glyphosate, is a highly effective and coimmercially important herbicide useful in controlling the growth of germinating seeds, emerging seedlings, maturing and established woody and herbaceous vegetation, and aquatic plants. Glyphosate is typically applied in the form of an aqueous solution of a salt thereof as a post-emergent herbicide for the control of growth of monocotyledonous and dicotyledonous plant species. Herbicidal salts of glyphosate and use thereof are described, for example, in U.S. Pat. No. 4,405,531.

Various methods for the production of glyphosate are known. For example, it can be produced by oxidizing N-phosphonomethyliminodiacetic acid in the presence of a catalyst. A variety of catalysts are known to catalyze such oxidation reactions. Glyphosate can also be produced by first reacting formylphosphonic acid (FPA) with glycine to form a condensation product and then hydrogenating the condensation product, for example, as described in U.S. Pat. No. 4,568,432. The latter synthetic route for glyphosate is desirable because a relatively high yield can be obtained. However, one limitation of this process is that the starting material, formylphosphonic acid, is not commercially available, and the methods known in the art for producing it suffers from one or more limitations.

For example, formylphosphonic acid is produced as a by-product in the electrochemical oxidation of nitrilotris-(methylenephosphonic acid) or substituted iminodimethyl-enediphosphonic acids to a secondary amine. This reaction requires the addition of a strong hydrochloric acid solution which presents safety, environmental, and equipment corrosion problems. Electrochemical methods generally require an external power source and other equipment which typically have higher maintenance needs and costs than non-electrochemical reactions.

Another known process in which formylphosphonic acid is produced as a by-product involves oxidation of tertiary phosphonomethylamines by oxygen in the presence of an activated carbon catalyst to cleave a phosphonomethyl group and to produce a secondary amine. Formylphosphonic acid may be produced as an intermediate cleavage fragment, with the fragment undergoing hydrolysis in a second step to form formic acid and phosphorous acid. Since a secondary amine is produced in the process, its presence necessitates additional steps, such as separation or recycling, which may result in manufacturing complexities.

Therefore, there exists a need for a new method for producing formylphosphonic acid and related compounds in an effective manner.

SUMMARY OF THE INVENTION

The aforementioned need is met by embodiments of the invention in one or more of the following aspects. In one aspect, the invention relates to a process of making a phosphorus-containing compound. The process comprises contacting a hydroxymethylphosphonic acid compound with an oxidant in the presence of a catalyst to produce a formylphosphonic acid compound or its hydrate. The hydroxymethylphosphonic acid compound is represented by Formula I below:

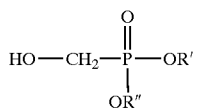

Formula I wherein R' and R" individually are hydrogen, hydrocarbyl, substituted hydrocarbyl, a salt-forming cation, or a heterocycle; the formylphosphonic acid compound is represented by Formula II below.

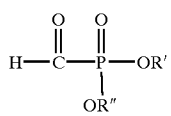

Formula II

In some embodiments, the oxidant is replenished during the contacting. The process may further comprise reacting the formylphosphonic acid compound with a nitrogen-containing compound represented by Formula III below

Formula III to produce a condensation product, wherein n is 0 or any positive integer, and R is —H, —OH, —CONH$_2$, —NH$_2$, —COOH, hydrocarbyl, substituted hydrocarbyl, a salt-forming cation, or a heterocycle, provided that when R is —COOH n is not zero. When n equals to 0 and R is —CONH$_2$, the nitrogen-containing compound is urea, and the condensation product is hydrogenated and converted to a glyphosate compound. When n equals to 1 and R is —COOR$_1$, the nitrogen containing compound is a primary amine represented by Formula IV:

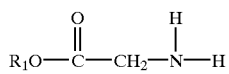

Formula IV wherein R$_1$, is hydrogen, hydrocarbyl, substituted hydrocarbyl, a salt-forming cation, or a heterocycle. In this embodiment, the process may further comprise hydrogenating the condensation product to produce a glyphosate compound represented by Formula V below.

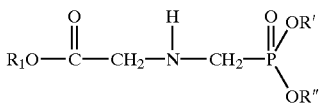

Formula V

When n equals to 0 and R is hydrogen, the nitrogen-containing compound is ammonia, and the condensation product is hydrogenated to form an aminomethylphosphonic acid compound represented by Formula VI below.

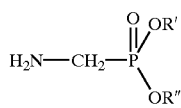

Formula VI

In this embodiment, the process may further comprise converting the aminomethylphosphonic acid compound to a glyphosate compound represented by Formula VII below.

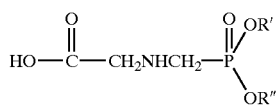

Formula VII

When n is 2 and R is —OH, the nitrogen-containing compound is ethanolamine, and the condensation product is hydrogenated to form a hydroxyethylaminomethylphosphonic acid compound represented by Formula VIII below.

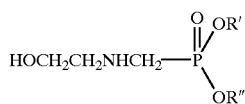

Formula VIII

In this embodiment, the hydroxyethylaminomethylphosphonic acid compound is oxidized to form a glyphosate compound represented by Formula VII. The glyphosate compound or one or more salts thereof so obtained may be admixed with one or more additives to produce a herbicidal formulation.

In some embodiments, the oxidant is $O_2$ or $H_2O_2$. Substantially pure oxygen, oxygen mixed with a carrier gas, or air may be used as an oxidant. In other embodiments, the hydroxymethylphosphonic acid compound is hydroxymethylphosphonic acid, and the formylphosphonic acid compound is formylphosphonic acid. The catalyst may be homogeneous, heterogeneous, supported, or unsupported. The catalyst may be an iron-containing compound, such as ferrous sulfate; a copper-containing compound, such as metallic copper, sponge copper, or Mo-doped copper; or a titanium-containing compound. The process may be conducted in the presence of a solvent, such as an aqueous solution or a non-aqueous solution. It may also be conducted in the presence of an acid or a base. The pH of the resulting mixture may be less than about 7, less than about 5, less than about 2, or less than about 1. The process may be conducted at a temperature of less than about 200° C., less than about 150° C., less than about 100° C., or less than about 50° C. In some embodiments, the oxidation reaction occurs electrochemically between the hydroxymethylphosphonic acid compound and the oxidant.

In another aspect, the invention relates to a process of making formylphosphonic acid. The process comprises contacting a hydroxymethylphosphonic acid with an oxidant in the presence of a catalyst to produce a formylphosphonic acid. The hydroxymethylphosphonic acid may be obtained by reacting formaldehyde with phosphorous acid. The oxidant may be $O_2$ or $H_2O_2$. The catalyst may be copper. In some embodiments, the oxidation reaction occurs electrochemically between the hydroxymethylphosphonic acid and the oxidant.

In still another aspect, the invention relates to a process of making glyphosate, a salt thereof, or a glyphosate precursor compound. The process comprises contacting a hydroxymethylphosphonic acid with oxygen or hydrogen peroxide in the presence of a catalyst to produce a formylphosphonic acid; and contacting the formylphosphonic acid with a reactant selected from the group consisting of ammonia, glycine, ethanolamine, and salts thereof to form a condensation product. When glycine or a salt thereof is used as the reactant, the condensation product is hydrogenated to form glyphosate or a salt thereof. When ammonia or a salt thereof is used as the reactant, the condensation product is hydrogenated to form aminomethylphosphonic acid or a salt thereof. The aminomethylphosphonic acid or a salt thereof may be carboxymethylated to form glyphosate or a salt thereof. When ethanolamine or a salt thereof is used as the reactant, the condensation product is hydrogenated to form hydroxyethylaminomethylphosphonic acid or a salt thereof. The hydroxyethylaminomethylphosphonic acid or salt thereof is oxidized to form glyphosate or a salt thereof The obtained glyphosate or one or more salts thereof may be admixed with one or more additives to produce a herbicidal formulation.

The hydroxymethylphosphonic acid may be obtained by reacting formaldehyde with phosphorous acid. The oxidant may be $O_2$ or $H_2O_2$. It may be substantially pure oxygen, oxygen mixed with a carrier gas, or air. The catalyst may be homogeneous, heterogeneous, supported, or unsupported. The catalyst may be an iron-containing compound, such as ferrous sulfate, a copper-containing compound, such as metallic copper, sponge copper, or Mo-doped copper, or a titanium-containing compound. The process may be conducted in an aqueous solution or a non-aqueous solution. It may be conducted in the presence of an acid or a base. The resulting mixture may have a pH of less than about 7, less than about 5, less than about 2, or less than about 1. The process may be conducted at a temperature of less than about 200° C., less than about 150° C., less than about 100° C., or less than about 50° C. In some embodiments, the oxidation reaction occurs electrochemically between the hydroxymethylphosphonic acid compound and the oxygen or hydrogen peroxide.

DESCRIPTION OF EMBODIMENTS OF THE INVENTION

Figure 1A:
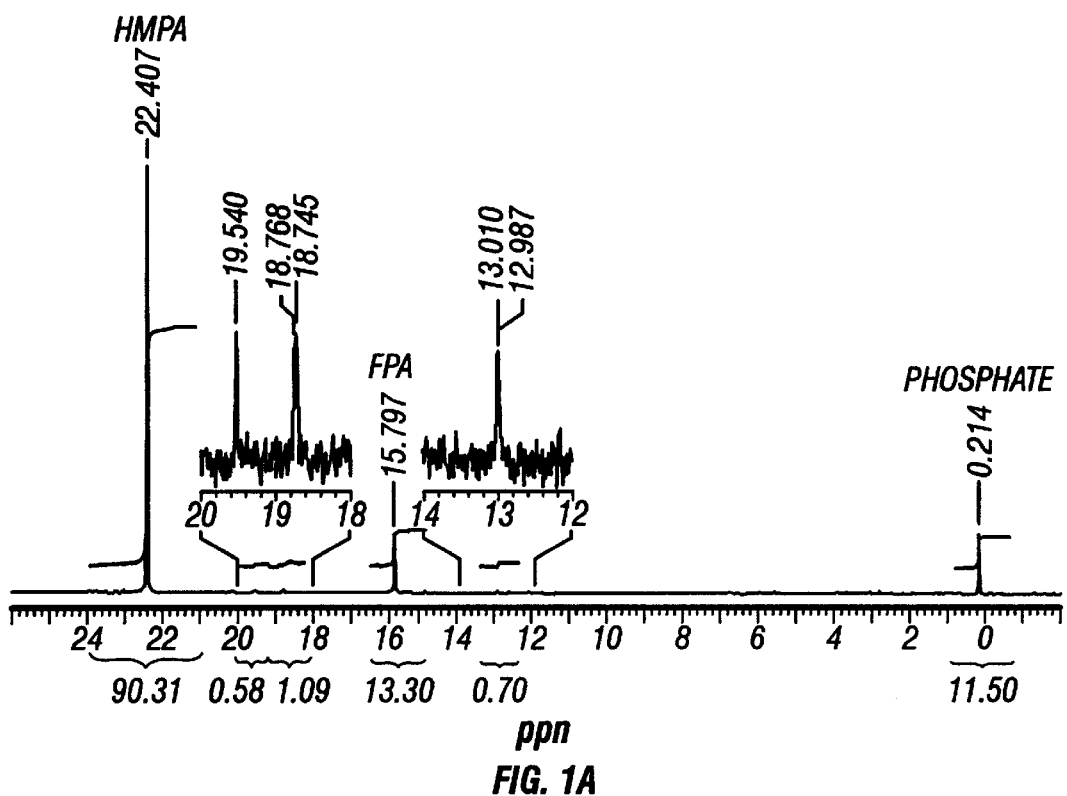
FIG. 1A is a proton-decoupled $^{31}$P NMR spectrum (121.4 MHz, $H_2O/D_2O$) for a reaction mixture prepared in accordance with one embodiment of the invention described in Example 3.

Embodiments of the invention are based, in part, on the discovery that the hydroxyl group of a hydroxymethylphosphonic acid compound can be selectively oxidized in the presence of a catalyst to an aldehyde group according to Scheme I illustrated in the following.

Scheme 1

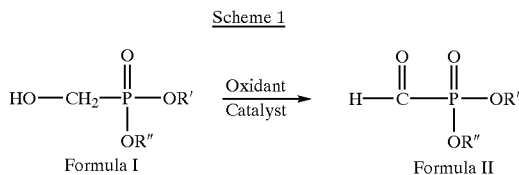

The hydroxymethylphosphonic acid compound is represented by Formula I, and the product which is a formylphosphonic acid compound is represented by Formula II. "Hydroxymethylphosphonic acid compound" refers to hydroxymethylphosphonic acid and its derivatives encompassed by Formula I. Similarly, "formylphosphonic acid compound" refers to fonnylphosphonic acid and its derivatives encompassed by Formula II. In the above formula, R' and R" individually can be hydrogen, hydrocarbyl, substituted hydrocarbyl, a salt-forming cation, or a heterocycle. Preferably, R' and R" both are hydrogen. In some embodiments, —OR' and —OR" each may be replaced by other organic or inorganic functional groups, such as halogen, —SH, —CN, heterocycle, —NO$_2$, amino, alkylamino, amido, etc.

The term "hydrocarbyl" refers to an organic group composed of carbon and hydrogen. It includes alkyl, alkenyl, and alkynyl groups which are each straight chain, branched chain, or cyclic hydrocarbons from one to about twenty carbons. Also included are aryl groups composed of carbon and hydrogen. For example, hydrocarbyl includes, but is not limited to, methyl, ethyl, propyl, butyl, pentyl, hexyl, cyclopropyl, cyclobutyl, cyclopentyl, cyclohexyl, methylcyclopentyl, ethenyl, propenyl, butenyl, pentenyl, hexenyl, ethyne, propyne, butyne, pentyne, hexyne, phenyl, naphthyl, anthracenyl, benzyl, and isomers thereof.

The term "substituted hydrocarbyl" refers to a hydrocarbyl group in which one or more hydrogen has been replaced with a heteroatom-containing group (which are also called "substituent groups"). Such substituent groups include, but are not limited to, —CN, halo, oxo, heterocycle, alkoxy, hydroxy, aryloxy, —NO$_2$, amino, alkylamino, amido, etc. When the substituent group is oxo, the substituted hydrocarbyl can be, for example, an acyl group. A suitable substituted hydrocarbyl group should be stable under the reaction conditions and does not interfere with the desired oxidation reaction. The term "heteroatom" refers to an atom of any element other than carbon or hydrogen which is capable of forming chemical bonds.

The term "heterocycle" refers to a saturated or unsaturated mono- or multi-ring carbocycle wherein one or more carbon atoms is replaced by N, S, P, or O. A heterocycle includes, for example, the following structures:

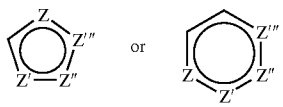

wherein Z, Z', Z", or Z'" is C, S, P, O, or N, with the proviso that one of Z, Z', Z", or Z'" is other than carbon, but is not O or S when attached to another Z atom by a double bond or when attached to another O or S atom. Furthermore, the optional substituents are understood to be attached to Z, Z', Z", or Z'" only when each is C. The point of attachment to the molecule of interest can be at the heteroatom or elsewhere within the ring. "Salt-forming cation" refers to any cation that forms a salt. For example, a salt-forming cation includes, but is not limited to, cations of alkali metals, alkaline earth metals, copper, zinc, manganese, nickel, ammonium, organic ammonium, etc.

Suitable oxidants for use in the reaction of Scheme I include any chemical reagent which is capable of oxidizing a hydroxyl group to an aldehyde group without further oxidizing all of the aldehyde produced. Preferably, a suitable oxidant does not substantially oxidize the aldehyde produced in the oxidation reaction. Preferred oxidants are oxygen and hydrogen peroxide. Either pure oxygen or air may be used. Molecular oxygen can also be diluted with an inert gas, such as nitrogen, helium, argon, etc. Hydrogen peroxide may be introduced as a pure liquid or in a mixture with a carrier. For example, a mixture of hydrogen peroxide and water may be used. Other oxidants may include, but are not limited to, ozone, singlet oxygen, nitrous oxide, organic peroxides, peracids, oxyhalides, etc. Additional oxidants may include, but are not limited to, chromic acid, Collin's reagent (chromium trioxide/pyridine), Corey's reagent (pyridinium chlorochromate), pyridinium dichlorochromate, dimethyl sulfoxide, tetrapropyl ammonium perruthemate, ceric ammonium nitrate, sodium dichromate in water, Ag$_2$CO$_3$/celite, oxygen/pyridine/CuCl, lead tetraacetate, lead acetate/pyridine, benzoyl peroxide/nickel bromide, MnO$_2$, etc.

Any catalyst which is capable of facilitating or catalyzing the oxidation reaction of Scheme I may be used in embodiments of the invention. For example, catalysts containing copper, iron, titanium, silver, palladium, platinum, or other metals may be used in embodiments of the invention. A preferred catalyst is a copper-containing compound. Suitable copper-containing compounds include, but are not limited to, metallic copper, copper alloys, copper nitrate, copper sulfate, copper carbonate, copper oxide, copper halide, copper hydroxide, copper formate, copper acetate, copper propionate, copper lactate, etc. A catalyst can be supported or unsupported. It may be used in any shape or form, such as powder, strips, plates, or in a solution. Any method for making a catalyst may be employed. For example, a suitable catalyst can be made by oxidizing a metallic copper surface followed by reduction; it can also be made by pyrolysis and/or reduction of copper formate or copper carbonate. Supported catalysts can be obtained by co-precipitation or submersion on a carrier. Examples of suitable carriers include, but are not limited to, alumina, silica-alumina, titanium oxide, zirconium oxide, silicon carbide, carbon, etc.

A preferred copper catalyst is sponge copper, such as Raney-brand copper ("Raney copper"). Raney copper is typically formed by selectively dissolving aluminum from a copper-aluminum alloy using sodium hydroxide, leaving highly-porous copper. The catalyst may have dopants added, either directly in the precursor alloy or in the leaching solution. Suitable dopants include any known metals or metallic alloys, including but not limited to, Mo, W, Cr, V, Nb, Ta, Ti, Zr, Y, Mn, Re, Se, Ru, Os, Co, Fe, Rh, Ir, Ni, Pd, Pt, Ag, Au, Zn, Cd, Hg, etc. In addition to sponge copper, other forms of copper with or without additives may be used.

The reaction according to Scheme I may be carried out at any temperature and pressure condition which produces the desired product. Typically, the oxidation reaction is carried out at a temperature ranging from about −50° C. to about 200° C. Preferably, it is carried out between about 0° C. and about 150° C., more preferably between about 25° C. and about 100° C. Generally, the reaction may be carried out under a pressure ranging from about 10 kPa (about 1.5 psi) to about 10,000 kPa (about 1500 psi). Preferably, the reaction is carried out under atmospheric pressure. When a gaseous oxidant is used, such as oxygen, the partial pressure of the gaseous oxidant may be any pressure which is consistent with the process equipment and produces the desired product. In some embodiments, the gaseous oxidant has a partial pressure in the range of about 7 kPa (about 1 psi) to about 3,500 kPa (about 500 psi). Other oxidation reaction conditions, such as those disclosed in U.S. Pat. No. 6,054,608 for oxidation of an aminomethylphosphonic acid substrate to produce formylphosphonic acid derivatives, also may be employed with or without modifications in embodiments of the invention. The disclosure of U.S. Pat. No. 6,054,608 is incorporated by reference in its entirety herein.

In addition, the oxidation reaction may be carried out electrochemically in any manner. For example, suitable methods for conducting electrochemical oxidation of organic compounds are described in *Organic Electrochemistry* (H. Lund and M. M. Baizer eds., Marcel Dekker, $3^{rd}$ ed. 1991). The conditions and apparatus for carrying out electrochemical oxidation disclosed in U.S. Pat. Nos. 3,835,000 and U.S. Pat. No. 4,568,432 may be used with or without modifications in embodiments of the invention. Both patents are incorporated by reference in their entirety herein.

Any molar ratio of the hydroxymethylphosphonic acid compound represented by Formula I to an oxidant may be used, for example, a molar ratio from about 0.01 to about 1000. Preferably, from about 0.2 to 1.5 equivalent of an oxidant is contacted with a hydroxymethylphosphonic acid compound. The hydroxymethylphosphonic acid compound may be contacted with an oxidant and a catalyst in any manner. The oxidation reaction may be conducted as a batch process, a continuous process, or any variation or combination thereof. Suitable reactors include any reactor capable of carrying out the oxidation reaction, such as a batch reactor, a continuous tube reactor packed with a heterogenous catalyst, and a fluidized bed reactor. For example, the hydroxymethylphosphonic acid compound can be placed in a closed container with some free space for containing a gaseous oxidant. Alternatively, a gaseous oxidant can be bubbled through a solution of a hydroxymethylphosphonic acid compound containing a suitable catalyst, either through a straight tube or a tube with a fritted diffuser attached thereto. If a liquid or solid oxidant is used, the oxidant may be added to a reactor either prior to or during the reaction in any manner.

A suitable catalyst may be used in any amount so long as it is sufficient to catalyze the oxidation of a hydroxymethylphosphonic acid compound. In other words, the disclosed oxidation reaction may be conducted in the presence of a catalytic amount of Raney copper or other suitable catalysts. Generally, the weight ratio of a hydroxymethylphosphonic acid compound to a catalyst may be in the range of about 0.001 to about 10,000 or more. For a homogenous catalyst, a preferred ratio may range from about 1 to about 10,000; in the case of a heterogenous catalyst, a preferred weight ratio may range from about 0.1 to about 100. The reaction may be carried out in the presence or absence of a solvent. Any solvent which is compatible with the process equipment and is stable under the reaction conditions may be used. Preferably, the solvent used should not interfere with the desired oxidation reaction. A suitable solvent may be aqueous or non-aqueous. Preferably, water is used as the solvent. In addition to water, other hydroxyl-containing compounds may also be used. Suitable solvents include, but are not limited to, alcohols, polyalcohols (such as ethylene glycol), polyethers (such as polyethylene glycol), acetic acid, tetrahydrofuran, dimethyl sulfoxide dioxane, acetonitrile, or a mixture thereof.

As discussed above, the oxidation reaction of Scheme I produces a formylphosphonic acid compound represented by Formula II. In the presence of a compound with a hyciroxyl group, such as water or alcohol, the formylphosphonic acid compound of Formula II may reversibly form the corresponding hemiacetal and/or acetal according to Scheme II shown below.

Scheme II

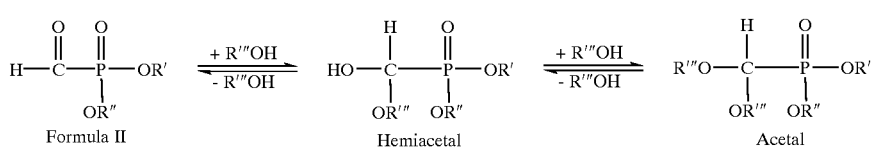

Formula II   Hemiacetal   Acetal

In the above reaction scheme, R'"—O—H represents any hydroxyl-containing compounds (e.g., water, alcohol, etc), wherein R'" is a monovalent functional group, such as hydrogen, hydrocarbyl, substituted hydrocarbyl, and a heterocycle. The hydroxymethylphosphonic acid compound of Formula I and the formylphosphonic acid compound of Formula II formed in the oxidation reaction may react according to Scheme II to form the corresponding hydrate, hemiacetal, or acetal. Under some reaction conditions, only the corresponding hydrate, hemiacetal, or acetal, instead of the formylphosphonic acid compound, is obtained as the final reaction product. However, the hydrate, hemiacetal, or acetal can be converted to the formylphosphonic acid if desired since the reactions are reversible.

The formylphosphonic acid compound of Formula II or its hydrate, hemiacetal, or acetal produced in embodiments of the invention has many useful applications. It may be used as an end product or an intermediate for making glyphosate or other valuable fine chemicals. Any method that converts FPA to a glyphosate compound in one or more steps may be used in embodiments of the invention. For example, a glyphosate compound may be produced by first reacting FPA with a nitrogen-containing compound to obtain a condensation product. The condensation product can then be converted to a glyphosate compound by one or more reactions, such as hydrogenation, carboxymethylation and/or oxidation. One class of suitable nitrogen-containing compounds is represented by Formula III:

Formula III in which n can be 0, 1, 2, 3, 4, 5, 6, or other positive integers; R is —H, —OH, —NH$_2$, —CONH$_2$, —CO$_2$H (provided that when R is —COOH, n is not zero), hydrocarbyl, substituted hydrocarbyl, a salt-forming cation, or a heterocycle. The nitrogen-containing compounds represented by Formula III can be reacted with formylphosphonic acid to produce glyphosate or other compounds. Preferably, n is 0, 1, or 2. When n is 0 and R is hydrogen or —CO—NH$_2$, the compound is ammonia or urea respectively. When n is 2 and R is —OH, the compound is ethanolamine. When n is 1 and R is —COOR, in which R$_1$ is hydrogen, hydrocarbyl, substituted hydrocarbyl, a salt-forming cation, or a heterocycle, the compound is a primary amine represented by formula IV below:

Formula IV

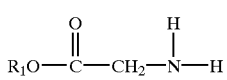

A wherein R$_1$ is hydrogen, hydrocarbyl, substituted hydrocarbyl, a salt-forming cation, or a heterocycle. Preferably, RI is hydrogen, and the primary compound is glycine. In some embodiments, secondary amines may be used in embodiments of the invention in a manner as described in U.S. Pat. No. 4,568,432.

The reaction between the formylphosphonic acid compound of Formula II and a primary amine or a salt thereof produces a condensation product. Upon hydrogenation, the condensation product is converted to a glyphosate compound represented by Formula V shown or salts thereof.

Formula V

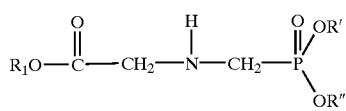

The above process for making glyphosate from FPA and a primary amine is described in U.S. Pat. No. 4,568,432, which is incorporated by reference in its entirety herein. The term "glyphosate compound" used herein refers to glyphosate (i.e., H$_2$O$_3$PCH$_2$NHCH$_2$CO$_2$H) and all its derivatives (including but not limited to all its salts) as represented by formula V. R$_1$ is defined in Formula IV, and R', and R" are defined in Formula I. In some embodiments, the —OR$_1$, —OR', and —OR" groups of formula V may be replaced by monovalent functional groups, such as halogen, —SH, amine, etc. The definition of "glyphosate compound" used herein encompasses all of the salts of N-phonphonomethylglycine disclosed in U.S. Pat. No. 4,405,531, which is incorporated by reference in its entirety herein. It further incorporates by reference the N-organo-N-phosphonomethylamino acetic acid compounds disclosed in U.S. Pat. No. 3,835,000.

One embodiment of the invention pertains to the preparation of glyphosate from hydroxymethylphosphonic acid as illustrated in Scheme III below.

Scheme III

H$_2$PO$_3$—CH$_2$—OH
(HMPA)

| oxidation

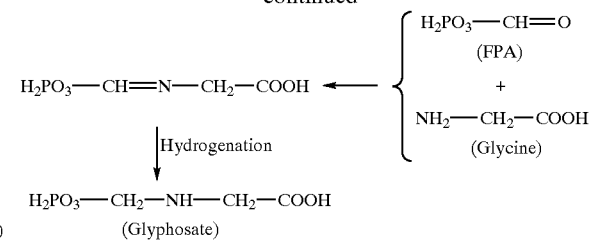

H$_2$PO$_3$—CH$_2$—NH—CH$_2$—COOH
(Glyphosate)

Hydroxymethylphosphonic acid ("HMPA") may be produced by any method. For example, HMPA can be prepared by reacting formaldehyde with phosphorus acid as disclosed in U.S. Pat. No. 5,266,722 and U.K. Patent Specification No. 1,076,244. U.S. Pat. No. 5,266,722 is incorporated by reference herein in its entirety. HMPA is treated with an oxidant in the presence of a catalyst as described above to afford formylphosphonic acid ("FPA"). FPA is then reacted with glycine to form a condensation product, which is subjected to hydrogenation to produce glyphosate. The condensation reaction and hydrogenation reaction may be conducted in any manner, such as the one described in U.S. Pat. No. 4,568,432. The glyphosate product may be separated from the reaction mixture according to known methods.

Instead of glycine, ammonia, its aqueous solution, or salts thereof may be used to react with FPA to form aminomethylphosphonic acid ("AMPA") or salts thereof. AMPA or salts thereof may be carboxymethylated, i.e., reacted in any manner and in any number of steps to introduce a carboxymethyl moiety to form glyphosate or salts thereof. This synthetic route from AMPA to glyphosate is illustrated in Scheme IV below.

Scheme IV

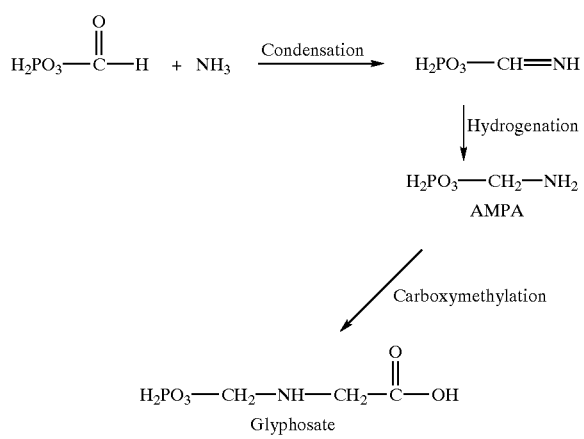

The carboxymethylation reaction may be conducted in any manner so long as the AMPA is converted to glyphosate in one or more steps. For example, the carboxymethylation processes described in U.S. Pat. No. 4,422,982 and Spanish Patent No.5,044,479 A3 may be used.

U.S. Pat. No. 4,422,982 is incorporated by reference in its entirety herein. Any carboxymethylating agent may be used, including but not limited to, monohaloacetic acid or a salt thereof, monohaloacetamide, etc. The halogen is fluorine, chlorine, bromine, or iodine.

Other processes for converting AMPA to glyphosate may also be used. For example, U.S. Pat. Nos. 4,369,142 and 4,486,358 disclose a method for preparation of glyphosate by reacting AMPA with glyoxal in an aqueous medium and in the presence of sulfur dioxide gas.

U.S. Pat. No 5,453,537 discloses a method for making glyphosate by reacting AMPA with a glyconitrile in the presence of an alkali metal hydroxide to afford a product and then hydrolyzing the product by adding an alkali metal hydroxide in an amount sufficient to neutralize the resulting carboxylic acid. U.S. Pat. Nos. 5,578,190 and 5,874,612 disclose a method for making glyphosate by condensing AMPA with glyoxylic acid or a related aldehyde compound and reducing the resulting condensation product. U.S. Pat. No. 5,679,843 and U.S. Pat. No. 5,948,937 disclose a method for making glyphosate by reacting AMPA, an alkali metal cyanide (or hydrogen cyanide), and formaldehyde to form N-phosphonomethylglycinonitrile and hydrolyzing the N-phosphonomethylglycinonitrile. All of these processes are carboxymethylation methods with the end result of the addition of the carboxymethyl moiety. The disclosures of all of the preceding patents are incorporated by reference in their entirety herein.

Another synthetic route from FPA to glyphosate is to react FPA with ethanolamine or salts thereof to form a condensation product. The condensation product may be hydrogenated to hydroxyethylaminomethylphosphonic acid ("HEAMPA") or salts thereof, which may be oxidized to glyphosate or salts thereof. Other suitable alkanolamines for producing useful compounds include, but are not limited to, 3-amino-1-propanol, 4-amino-1-butanol, 5-amino-1-pentanol, 6-amino-1-hexanol, etc. Scheme V below illustrates the synthetic route from FPA to glyphosate in which ethanolamine is reacted with FPA.

phosate produced in accordance with embodiments of the invention can be utilized in a manner disclosed in the above patents. The disclosures of all of the preceding U.S. patents are incorporated by reference in their entirety herein.

EXAMPLES

The following examples are given to illustrate various embodiments of the invention. They should not be construed to limit the invention as otherwise described and claimed herein. All numbers are approximate values, and variations from the specified values are acceptable.

Reaction Apparatus—Unless otherwise indicated, the oxidation reactions were performed in a 300-mL hastelloy-C Autoclave Engineer's autoclave equipped with hastelloy-C wetted parts. Oxygen was introduced into the reactor via sintered metal frit below a standard six-bladed radial impeller turning at 900 rpm. Oxygen was metered into the vessel using a Brooks Model 5850 mass flow controller, and reactor pressure was maintained by a Tescom Model 25-1727 back-pressure regulator. Gas flow exiting the reactor was monitored by a Brooks Model 5860 mass flow meter, and liquid sampling was accomplished through a separate sintered metal frit. Reactor temperature was controlled using a Love Model 32120-524 PID controller. Reactor data (e.g., temperature, pressure, and flows) was logged with a IBM-compatible computer. Three types of copper were used as catalysts: Cu power (i.e., copper purified electrolytic dust) from Fisher Scientific, 5–10 $\mu$m copper powder from Aldrich Chemical, and Raney copper from Kawaken Chemical.,

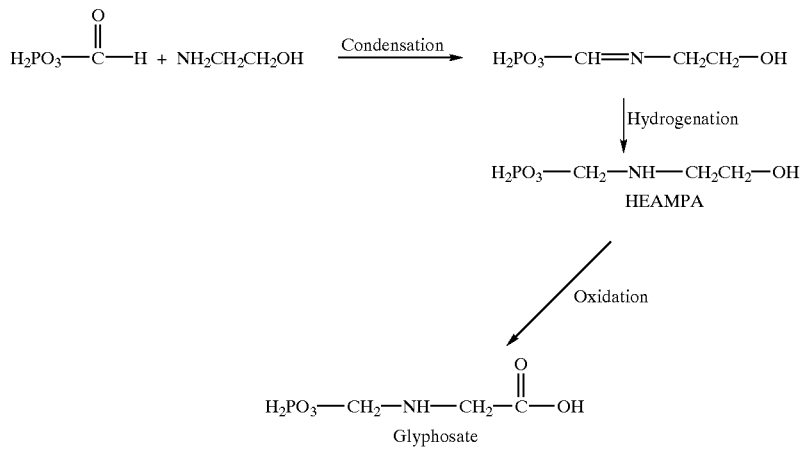

Scheme V

The oxidation of HEAMPA to form glyphosate may be carried out in any manner. For example, HEAMPA may be oxidized by the oxidation processes described herein. It may also be oxidized according to the methods as described in U.S. Pat. Nos. 4,810,426, 5,292,936, and 5,602,276, which are incorporated by reference in their entirety herein.

Forcommerical applications, glyphosate is generally employed in the form of a salt in which the cation is, for example, an alkali metal, an alkaline earth metal, ammonium, or an organic ammonium in herbicide formulations. The following U.S. patents disclose methods of making and using herbicide formulations for various applications: U.S. Pat. Nos. 3,799,580; 3,853,530; 3,977,860; 3,988,142; 4,140,513; 4,315,765; 4,405,531; 4,481,026; 4,507,250; 4,840,659; 5,693,593; 5,912,209; 5,935,905; 5,985,794; 5,994,269; 5,998,332; and 6,083,878. The gly- Ltd., Japan. The Raney copper catalyst used contained about 3500 ppm Mo.

Preparation of HMPA—A solution of phosphorous acid (500.0 g, 6.10 mol), aqueous formaldehyde (37 wt %, 940.0 g, 11.6 mol), and concentrated HCl (12 N, 75 mL) was distilled to remove volatiles (bp <80° C.) and then heated at reflux for 108 hours. After concentration of the reaction mixture to 774 g by rotary evaporation, crystals began forming upon standing at room temperature. The crystals were isolated by filtration on a sintered glass frit and washed extensively with ethyl acetate (10×200 mL). Volatiles were removed in vacuo at 40–50° C. for several days to afford 278.7 g (40.8%) of HMPA as a white crystalline powder. mp 96–98 ° C. $^{31}$P NMR (121.4 MHz, D$_2$O) δ 22.6 ppm.

Analysis of Reaction Products—all formylphosphonic acid (FPA) analyses, unless otherwise indicated, were performed by $^{31}$P NMR on a Varian Unity 300 at 121.4 MHz. All NMR spectra were obtained from $D_2O$ or $H_2O/D_2O$ solutions. $^{31}$P chemical shifts are reported as positive values downfield from 85% $H_3PO_4$. FPA yield and selectivity and HMPA conversion were calculated on the basis of normalized $^{31}$P NMR peaks. For an aliquot of a reaction mixture, their normalized $^{31}$P NMR peak areas for HMPA, FPA, $H_3PO_3$, and $H_3PO_4$ were measured. Calculations were performed according to the following equations.

$$FPA\ yield = \frac{[FPA]}{[HMPA] + [FPA] + [H_3PO_3] + [H_3PO_4]}$$

$$FPA\ selectivity = \frac{[FPA]}{[FPA] + [H_3PO_3] + [H_3PO_4]}$$

$$HMPA\ conversion = \frac{[FPA] + [H_3PO_3] + [H_3PO_4]}{[HMPA] + [FPA] + [H_3PO_3] + [H_3PO_4]}$$

The normalized $^{31}$P NMR peak area was used to represent the relative molar concentration of the respective compounds.

Example 1

The autoclave described above was charged with Raney copper (4.50 g, 0.071 mol) and HMPA (23.06 g, 0.2059 mol) dissolved in deionized water (100 g). The reactor was pressurized to 150 psig with nitrogen, mechanically stirred at 900 rpm and heated to 100° C. When the reactor contents reached 100° C., oxygen was introduced at 100 sccm. The reactor was sampled soon after net gas consumption ended after 30 min of oxygen inlet flow. Oxygen flow was terminated and cooling was initiated after a total of 60 min of oxygen input. Aliquots of the interim and final reaction mixtures were passed through a plug of Dowex 50W×8–400 ion exchange resin (H$^+$ form) to remove paramagnetic species. Analysis was performed by $^{31}$P NMR. Results are summarized in Table 1.

TABLE 1

Results of $^{31}$P {$^1$H} NMR analysis of the oxidation of HMPA at 100° C. and 150 psig with 100 sccm oxygen input.

| Compound | @ 30 min (end of gas uptake) | @ 60 min (end of run) |
| --- | --- | --- |
| HMPA | 82 mol % | 81 mol % |
| FPA | 10 mol % | 9 mol % |
| PO$_4$ | 8 mol % | 10 mol % |

Example 2

The autoclave was charged as described in Example 1 and heated to 75° C. at which point 50 sccm oxygen was fed into the reaction mixture. A sample was removed after 75 min of input flow corresponding to the end of net gas consumption. The aliquot was treated as described in Example 1. Analysis by $^{31}$P NMR revealed 21% conversion of HMPA with 65% selectivity to FPA.

Example 3

A reaction was carried out in the same manner as Example 1 except that the oxygen addition rate was at 50 sccm (half of that of Example 1). The results are summarized in Table 2.

TABLE 2

Results of $^{31}$P {$^1$H} NMR analysis of the oxidation of HMPA at 100° C. and 150 psig with 50 sccm oxygen input

| Compound | @ 65 min (end of gas uptake) | @ 130 min (end of run) |
| --- | --- | --- |
| HMPA | 78 mol % | 78 mol % |
| FPA | 12 mol % | 9 mol % |
| PO$_4$ | 10 mol % | 14 mol % |

Figure 1B:
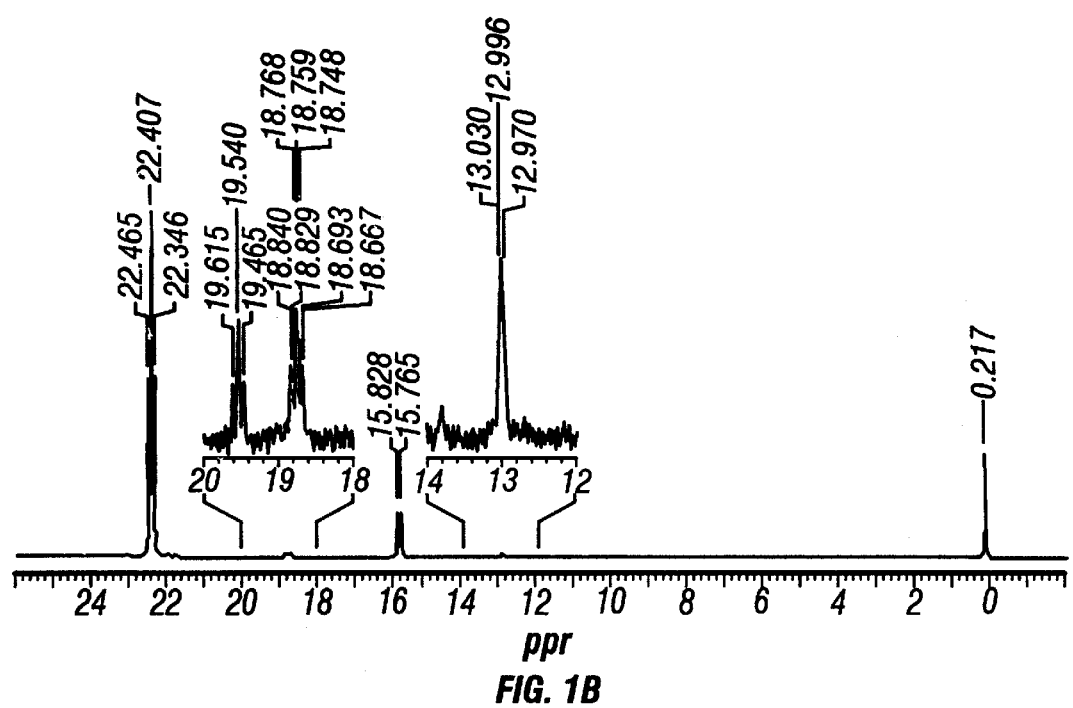
FIG. 1B is a proton-coupled $^{31}$P NMR spectrum (121.4 MHz, $H_2O/D_2O$) for the reaction mixture of FIG. 1A.

Two NMR spectra of the interim aliquot obtained in this example are shown in FIG. 1. Specifically, FIG. 1A is a proton-decoupled $^{31}$P NMR spectrum of the aliquot. The chemical shifts corresponding to phosphate, FPA, and HMPA are indicated respectively. In addition, several small peaks around 13 ppm and 18 ppm were also observed. Extreme magnification of these peaks reveal a doublet in the proton-decoupled $^{31}$P NMR spectrum indicating P-P coupling. FIG. 1B is a proton-coupled $^{31}$P NMR spectrum of the same aliquot. The proton-coupled spectrum shows that the doublets are further split by a proton to an apparent triplet of doublets and an apparent doublet of doublets, respectively. Though not well resolved, the P-P coupling is about 3 Hz and the H-P couplings are about 9 Hz and 3 Hz, respectively, for the two resonances. This coupling behavior is consistent with the formation of formylphosphonic acid HMPA hemiacetal (FHA) from the reaction of FPA with unreacted HMPA.

Example 4

The autoclave was charged with purified copper powder (4.5 g, electrolytic dust, Fisher Scientific), HMPA (23.03 g, 0.2056 mol), and 100 g deionized water. The oxidation was then performed as described in Example 1 at 100° C. and 50 sccm oxygen input with net gas consumption lasting about 60 min. A sample taken after 70 min was treated and analyzed as described in Example 1. The results showed 18% conversion of HMPA with 30% selectivity to FPA.

Example 5

Two reactions were carried out in a manner similar to Example 1 except as otherwise indicated. The reactions involved HMPA (23.0 g, 0.205 mol) and copper (4.5 g, 0.071 mol) in water (ca 100 g) with oxygen at 150 psig. Conversion and reaction selectivity to FPA are based on $^{31}$P NMR analysis of the product solution after removal of Cu(II) by passing the final reaction mixture through a plug of Dowex 50W×8 (H$^+$ form). The results are summarized in Table 3.

TABLE 3

FPA Yield and Selectivity as a Function of Reaction Temperature

| catalyst | temp ° C. | O$_2$ flow sccm | rxn time | HMPA conversion | selectivity | FPA yield |
| --- | --- | --- | --- | --- | --- | --- |
| Raney Cu | 75 | 50 | 72 min | 21% | 65% | 14% |
| Raney Cu | 50 | 50 | 73 min | 25% | 62% | 15% |

A 250-mL three-necked round bottom flask was charged with Raney copper (4.5 g), HMPA (23.03 g, 0.2056 mol), and 10 g deionized water. The mixture was heated to 75° C. under an atmosphere of nitrogen with stirring. Aqueous hydrogen peroxide (30 wt %, 24.0 g, 0.211 mol) was added over a 105 min period and then the completed reaction mixture was stirred at 75° C. for an additional 180 min.

Aliquots of the reaction mixture were removed after about 15% of the $H_2O_2$ had been added, after peroxide addition was complete, and at the end of the 180 min period. Samples were treated with the ion exchange resin as described in Example 1 and analyzed by $^{31}P$ NMR. The results of the analyses are summarized in Table 4.

TABLE 4

Results of $^{31}P$ {$^1H$} NMR analysis of the oxidation of HMPA at 75° C. with hydrogen peroxide.

| compound | after 15% $H_2O_2$ added | after complete $H_2O_2$ addition | final mixture |
|---|---|---|---|
| HMPA | 89 mol % | 49 mol % | 50 mol % |
| FHA[a] | not detected | 1 mol % | 1 mol % |
| FPA | 6 mol % | 14 mol % | 12 mol % |
| $H_3PO_3$ | not detected | 4 mol % | 5 mol % |
| $H_3PO_4$ | 3 mol % | 30 mol % | 32 mol % |

[a]compound tentatively identified as the FPA-HMPA hemiacetal

Example 7

Two reactions were carried out in a manner similar to Example 1 except as otherwise indicated. Different amounts of HMPA were used: 11.5 g and 46.2 g of HMPA mixed with copper (5.1 g, 0.080 mol) in water (ca. 109 g) with 50 sccm oxygen at 150 psig. The reactions were carried about 75° C. Results relating to conversion and reaction selectivity to FPA were based on $^{31}P$ analysis of the product solution after removal of Cu(II) by passing an aliquot of the reaction mixture through a plug of Dowex 50W×8 (H$^+$ form). The results are summarized in Table 5.

TABLE 5

| HMPA added | [HMPA]$_i$ wt % | rxn time[a] | HMPA conversion: % of initial (grams) | selectivity | product solution pH |
|---|---|---|---|---|---|
| 11.5 g | 10% | 55 min | 28% (3.22 g) | 46% | 2.73 |
| 46.2 g | 30% | 73 min | 14% (6.47 g) | 65% | 0.82 |

[a]Time from initiation of oxygen input until net gas exit flow returned to match that of the feed.

Example 8

A series of reactions were carried out in a manner similar to Example 6 except as otherwise indicated. All reactions involved 23.0 g (0.21 mol) of HMPA, 4.5 g (0.071 mol) of metallic copper in 100 g of water under nitrogen. Hydrogen peroxide (30%, 23.8 g, 0.21 mol) was metered in via a peristaltic pump over 1.6–1.75 hr, and aliquots were removed for analysis ($^{31}P$ NMR) at perodic intervals during the course of the addition. The results are summarized in Table 6.

TABLE 6

HMPA Oxidation by Hydrogen Peroxide.

| run number | catalyst | temp. ° C. | maximum observed FPA yield | maximum FPA yield was observed when |
|---|---|---|---|---|
| 1 | Cu powder | 50 | 21% | 64% of the stoichiometric amount of $H_2O_2$ was added |
| 2 | Cu powder | 25 | 27% | 100% of the stoichiometric amount of $H_2O_2$ was added |
| 3 | Cu powder | 5 | 31% | 86% of the stoichiometric amount of $H_2O_2$ was added |
| 4 | Cu powder (5–10 μm) | 25 | 29% | 86% of the stoichiometric amount of $H_2O_2$ was added |
| 5 | Raney Cu | 50 | 18% | 66% of the stoichiometric amount of $H_2O_2$ was added |
| 6 | Raney Cu | 5 | 24% | 86% of the stoichiometric amount of $H_2O_2$ was added |

Figure 2:
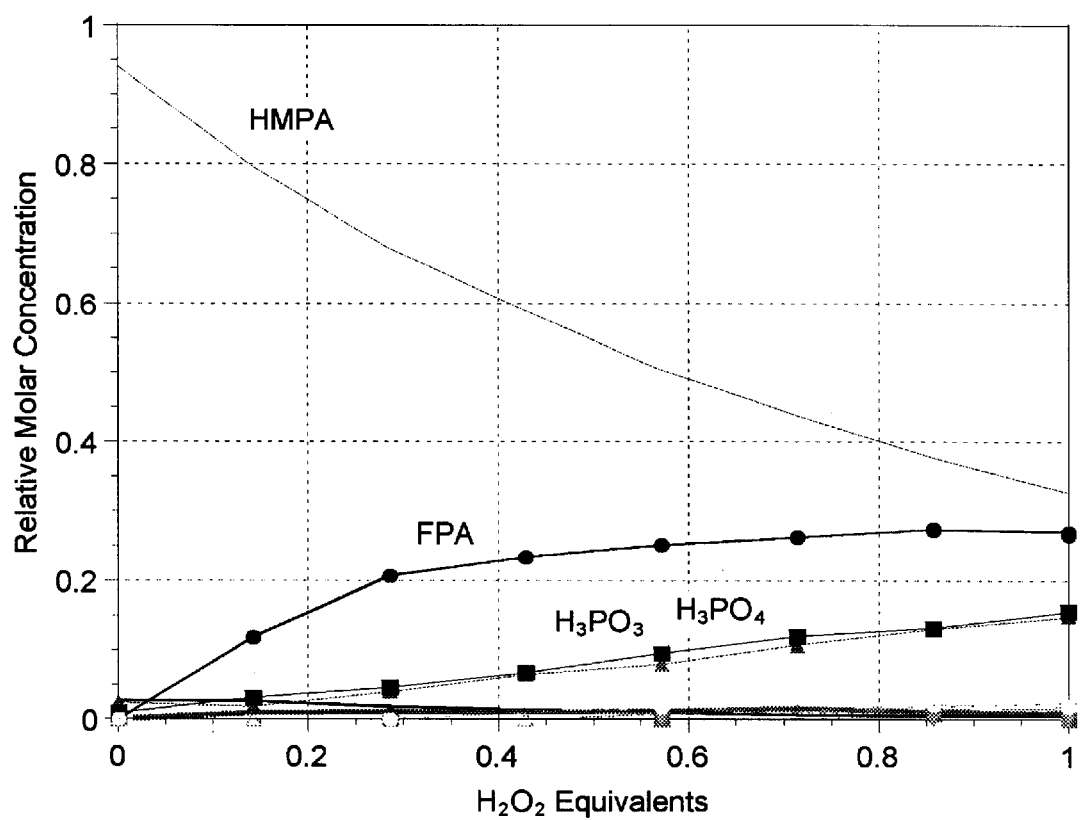
FIG. 2 is a product file of an oxidation reaction of hydroxymethylphosphonic acid with hydrogen peroxide in accordance with another embodiment of the invention described in Example 8.

FIG. 2 shows the time profile for Run No. 3 as expressed in terms of $H_2O_2$ equivalents.

Example 9

A series of reactions were carried out to study the effect of pH on oxidation of A 250-mL round bottom flask equipped with a condenser, magnetic stirrer, and thermcouple was charged with 23.0 g of HMPA and 4.5 g of copper electrolytic dust. Also added respectively to the flask was 100 mL of deionized water, 100 mL of an aqueous $H_2SO_4$ solution, or 100 mL of an aqueous NaOH solution. The stirred mixture was heated to 50° C. at which time air was introduced into the solution via a sintered glass gas dispersion tube. Aliquots were removed periodically and analyzed by $^{31}P$ NMR. The results are summarized in Table 7. The results suggest that more acidic conditions improve FPA formation.

TABLE 7

Copper catalyzed oxidations of HMPA with air and the addition of acid or base. Air sparging of the reaction mixture continued at least until the metallic copper catalyst had dissolved.

| temp | Rxn time | acid or base added | conversion | FPA select. | FPA yield | product solution pH |
|---|---|---|---|---|---|---|
| 50° C. | 6.00 hr | 1.0 eq. $H_2SO_4$ | 30% | 92% | 27% | −0.3 |
| 50° C. | 6.00 hr | 0.5 eq. $H_2SO_4$ | 26% | 80% | 21% | 0.3 |
| 50° C. | 5.25 hr | 0.2 eq. $H_2SO_4$ | 23% | 78% | 18% | 0.9 |
| 50° C. | 3.75 hr | 0.5 eq. NaOH | 15% | 75% | 11% | 1.8 |
| 50° C. | 3.00 hr | 1.0 eq. NaOH | 4% | 68% | 3% | 5.1 |

Example 10

A series of reactions were carried out under conditions similar to those of Example 6, except that an acid (e.g., sulfuric acid) was added to the reactor. The results are summarized in Table 8 below.

TABLE 8

Copper catalyzed oxidations of HMPA with 1 eq. hydrogen peroxide with the addition of an acid.

| temp | Rxn time | acid added | conversion | FPA select. | FPA yield |
|---|---|---|---|---|---|
| 25° C. | 2.78 hr | 1.0 eq. $H_2SO_4$ | 66% | 50% | 33% |
| 50° C. | 3.77 hr | 1.0 eq. $H_2SO_4$ | 58% | 58% | 34% |
| 25° C. | 0.33 hr | 0.5 eq. $H_2SO_4$ | 64% | 48% | 31% |

TABLE 8-continued

Copper catalyzed oxidations of HMPA with 1 eq. hydrogen peroxide with the addition of an acid.

| temp | Rxn time | acid added | conversion | FPA select. | FPA yield |
|---|---|---|---|---|---|
| 50° C. | 1.67 hr | 0.5 eq. H$_2$SO$_4$ | 59% | 56% | 33% |
| 50° C. | 1.70 hr | none | 55% | 53% | 29% |

As demonstrated above, embodiments of the invention provide a process for making certain phosphorus-containing compounds represented by Formula II, V, and derivatives thereof These compounds can be used as an end product or an intermediate for making additional products. In particular, the embodiments of the invention provide a new process for making FPA and glyphosate. Such a process may offer one or more of the following advantages. First, because FPA is produced from HMPA which, in turn, may be obtained by reacting formaldehyde with phosphorus acid, the raw material costs are relatively lower. Due to the relative simplicity of the chemistries involved, the method may be easily implemented on a commercial scale. Moreover, it is possible to design a continuous reactor to produce glyphosate in one or two steps. This may result in substantial reduction in the cost of manufacturing glyphosate. The oxidation of HMPA to yield FPA can be carried out at ambient temperature and pressure in which air is utilized as the oxidant. This should result in additional cost savings. Additional advantages provided by embodiments of the invention are apparent to those skilled in the art.

While the invention has been described with a limited number of embodiments, the scope of the invention is not intended to be limited by the specific embodiments. Moreover, modifications and variations from the described embodiments exist. For example, because the formylphosphonic acid compound of Formula II may undergo a further reaction to yield the corresponding hydrate, hemiacetal and/or acetal compound, the formylphosphonic acid compound TzE of Formula II may not be present or detectable in the oxidation reaction of Scheme I under certain conditions. As such; the formation of a hydrate, hemiacetal and/or acetal of a formylphosphonic acid compound is considered as equivalent to the formation of the formylphosphonic acid compound. Although suitable oxidants and catalysts are exemplified by a number of specific compounds, they do not represent an exclusive list of suitable oxidants and catalysts. Other catalysts and oxidants which are not listed herein may still be used in embodiments of the invention. The methods disclosed herein are described with reference to a number of steps. These steps may be practiced in any sequence, and two or more steps may be practiced simultaneously. While FPA is described as an intermediate for making glyphosate, its application is not so limited. For example, formylphosphonic acid can alternatively be used as an advanced intermediate in the preparation of medicinally important compounds such as the antiviral agent phosphono hydroxyacetic acid. As a reagent or intermediate, formylphosphonic acid has potential for chemical reactions at the carbonyl, phosphorus, or hydroxyl moieties. While the presence of FPA in the reaction mixture is identified by $^{31}$P NMR spectroscopy, this does not preclude the use of any other analytical techniques to identify FPA. Finally, any number of oxidants and catalysts may be used in embodiments of the reaction. The appended claims intend to cover all such modification and variations as falling within the scope of the invention.

What is claimed is:

1. A process of making a phosphorus-containing compound, of formula (II) comprising:

contacting a hydroxymethylphosphonic acid compound of formula I with an oxidant in the presence of a catalyst to produce a formylphosphonic acid compound or formula II its hydrate, wherein the hydroxymethylphosphonic acid compound is represented by Formula I:

Formula I

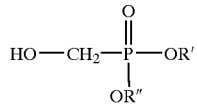

wherein R' and R" individually are hydrogen, hydrocarbyl, substituted hydrocarbyl, a salt-forming cation, or a heterocycle; and wherein the formylphosphonic acid compound is represented by Formula II.

Formula II

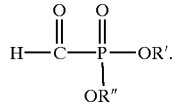

2. The process of claim 1, wherein the oxidant is replenished during the contacting.

3. The process of claim 1, further comprising reacting the formylphosphonic acid compound with a nitrogen-containing compound represented by Formula III Formula III

to produce a condensation product, wherein n is 0 or any positive integer, and R is —H, —OH, —CONH$_2$, —NH$_2$, —COOH, hydrocarbyl, substituted hydrocarbyl, a salt-forming cation, or a heterocycle, provided that when R is —COOH n is not zero.

4. The process of claim 3, wherein when n is 0 and R is —CONH$_2$, the nitrogen-containing compound is urea, and the condensation product is hydrogenated and converted to a glyphosate compound.

5. The process of claim 3, wherein when n is 1 and R is —COOR$_1$, the nitrogen-containing compound is a primary amine represented by Formula IV:

Formula IV

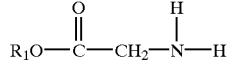

wherein R$_1$ is hydrogen, hydrocarbyl, substituted hydrocarbyl, a salt-forming cation, or a heterocycle.

6. The process of claim 5, further comprising hydrogenating the condensation product to produce a glyphosate compound represented by Formula V.

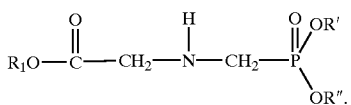

Formula V

7. The process of claim 3, wherein n is 0 and R is hydrogen, the nitrogen-containing compound is ammonia, and the condensation product is hydrogenated to form an aminomethylphosphonic acid compound represented by Formula VI.

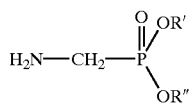

Formula VI

8. The process of claim 7, further comprising converting the aminomethylphosphonic acid compound to a glyphosate compound represented by Formula VII:

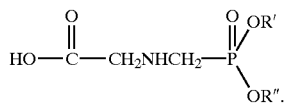

Formula VII

9. The process of claim 3, wherein n is 2 and R is —OH, the nitrogen-containing compound is ethanolamine, and the condensation product is hydrogenated to form a hydroxyethylaminomethylphosphonic acid compound represented by Formula VIII.

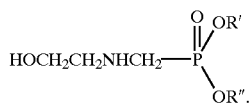

Formula VIII

10. The process of claim 9, wherein the hydroxyethylaminomethylphosphonic acid compound is oxidized to form a glyphosate compound represented by Formula VII.

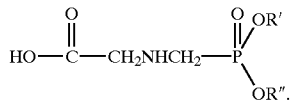

Formula VII

11. The process of claim 6, further comprising admixing the glyphosate compound or one or more salts thereof with one or more additives to produce a herbicidal formulation, wherein at least one of $R_1$, R', and R" is hydrogen.

12. The process of claim 8, further comprising admixing the glyphosate compound or one or more salts thereof with one or more additives to produce a herbicidal formulation.

13. The process of claim 10, further comprising admixing the glyphosate compound or one or more salts thereof with one or more additives to produce a herbicidal formulation.

14. The process of claim 1, wherein the oxidant is $O_2$ or $H_2O_2$.

15. The process of claim 14, wherein the oxidant is a substantially pure oxygen gas.

16. The process of claim 14, wherein the oxidant is oxygen gas mixed with a carrier gas.

17. The process of claim 14, wherein the oxidant is air.

18. The process of claim 1, wherein the hydroxymethylphosphonic acid compound is hydroxymethylphosphonic acid.

19. The process of claim 1, wherein the formylphosphonic acid compound is formylphosphonic acid.

20. The process of claim 1, wherein the catalyst is homogeneous.

21. The process of claim 1, wherein the catalyst is heterogeneous.

22. The process of claim 21, wherein the catalyst is supported.

23. The process of claim 1, wherein the catalyst is an iron-containing compound.

24. The process of claim 23, wherein the catalyst is ferrous sulfate.

25. The process of claim 1, wherein the catalyst is a copper-containing compound.

26. The process of claim 25, wherein the catalyst is metallic copper.

27. The process of claim 25, wherein the catalyst is sponge copper.

28. The process of claim 25, wherein the catalyst is Mo-doped copper.

29. The process of claim 1, wherein the catalyst is a titanium-containing compound.

30. The process of claim 1, wherein the process is conducted in the presence of a solvent.

31. The process of claim 1, wherein the process is conducted in an aqueous solution.

32. The process of claim 1, wherein the process is conducted in a non-aqueous solution.

33. The process of claim 1, wherein the process is conducted in the presence of an acid.

34. The process of claim 1, wherein the process is conducted in the presence of a base.

35. The process of claim 33, wherein the pH of the resulting mixture is less that about 7.

36. The process of claim 33, wherein the pH of the resulting mixture is less that about 5.

37. The process of claim 33, wherein the pH of the resulting mixture is less that about 2.

38. The process of claim 33, wherein the pH of the resulting mixture is less that about 1.

39. The process of claim 1, wherein the process is conducted at a temperature of less than about 200°C.

40. The process of claim 1, wherein the process is conducted at a temperature of less than about 150° C.

41. The process of claim 1, wherein the process is conducted at a temperature of less than about 100° C.

42. The process of claim 1, wherein the process is conducted at a temperature of less than about 50° C.

* * * * *

UNITED STATES PATENT AND TRADEMARK OFFICE
CERTIFICATE OF CORRECTION

PATENT NO.    : 6,441,223 B1
DATED         : August 27, 2002
INVENTOR(S)   : Thaddeus S. Franczyk, II It is certified that error appears in the above-identified patent and that said Letters Patent is hereby corrected as shown below:

Title page,
Item [56], OTHER PUBLICATIONS, replace "[M1x; MxFe, Cu, Co, Mn]" with -- [M1x; M=Fe, Cu, Co, Mn] --

Column 1,
Line 25, replace "coimmercially" with -- commercially --

Column 4,
Line 59, replace "aproduct" with -- a product --

Column 5,
Line 19, replace "fonnylphosphonic" with -- formylphosphonic --

Column 7,
Line 57, replace "areactor" with -- a reactor --

Column 8,
Line 20, replace "hyciroxyl" with -- hydroxyl --

Column 9,
Line 8, replace "- COOR," with -- -COOR$_1$ --
Line 21, replace "RI" with -- R$_1$ --

Column 10,
Lines 35-37, Replace "H$_2$PO$_3$–C–H" (with =O double bond on C)

With --"H$_2$PO$_3$–C–H"-- (with =O double bond on C)
FPA

Column 11,
Line 58, replace "Forcommerical" with -- For commercial --

Column 14,
Line 36, replace "perfonned" with -- performed --
Line 63, replace "10" with -- 110 --

UNITED STATES PATENT AND TRADEMARK OFFICE
CERTIFICATE OF CORRECTION

PATENT NO.     : 6,441,223 B1
DATED          : August 27, 2002
INVENTOR(S)    : Thaddeus S. Franczyk, II It is certified that error appears in the above-identified patent and that said Letters Patent is hereby corrected as shown below:

Column 15,
Line 27, replace "The reactions were carried about 75º C."
with -- The reactions were carried out at about 75º C --
Line 50, replace "matered" with -- metered --
Line 52, replace "perodic" with -- periodic --

Column 16,
Line 23, replace "oxidation of A" with -- oxidation of HMPA.  A --

Column 17,
Line 40, delete "TzE" before -- "of formula II" --
Line 42, replace ";" with -- , --

Column 18,
Line 3, replace "compound, of formula (II) comprising:"
with -- compound of formula (II), comprising: --
Lines 8-9, replace "catalyst to produce a formylphosphonic acid compound or formula II its hydrate," with -- catalyst to produce a formylphosphonic acid compound of formula II or its hydrate, --

Column 20,
Line 59, add -- 43. The process of claim 1, wherein an oxidation reaction occurs electrochemically between the hydroxymethyl phosphonic acid compound and the oxidant --

Signed and Sealed this

Eighteenth Day of February, 2003

JAMES E. ROGAN
*Director of the United States Patent and Trademark Office*